(12) United States Patent
Kilaz et al.

(10) Patent No.: US 11,513,104 B2
(45) Date of Patent: Nov. 29, 2022

(54) METHODS FOR CLASSIFICATION OF HYDROCARBON MIXTURES

(71) Applicant: Purdue Research Foundation, West Lafayette, IN (US)

(72) Inventors: Gozdem Kilaz, West Lafayette, IN (US); Petr Vozka, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 336 days.

(21) Appl. No.: 16/727,900

(22) Filed: Dec. 26, 2019

(65) Prior Publication Data

US 2020/0132640 A1 Apr. 30, 2020

Related U.S. Application Data

(60) Provisional application No. 62/751,331, filed on Oct. 26, 2018.

(51) Int. Cl.
*G01N 30/68* (2006.01)
*G01N 33/28* (2006.01)
*G01N 30/86* (2006.01)

(52) U.S. Cl.
CPC ......... *G01N 30/68* (2013.01); *G01N 30/8696* (2013.01); *G01N 33/28* (2013.01)

(58) Field of Classification Search
None
See application file for complete search history.

(56) References Cited

U.S. PATENT DOCUMENTS

| 2009/0282897 A1* | 11/2009 | Bertoncini | G01N 33/2811 |
| | | | 73/23.38 |
| 2015/0107331 A1* | 4/2015 | Wang | G01N 30/7206 |
| | | | 73/23.37 |
| 2016/0363569 A1* | 12/2016 | Walsh | G01N 30/8686 |
| 2018/0143168 A1* | 5/2018 | Wang | G01N 30/6034 |

OTHER PUBLICATIONS

Vozka, P. et al., "Middle Distillates Hydrogen Content Via GC x GC-FID", Talanta, vol. 186, 2018, pp. 140-146.*
Striebich, R.C. et al., "Hydrocarbon Group-Type Analysis of Petroleum-Derived and Synthetic Fuels Using Two-Dimensional Gas Chromatography", Energy Fuels, vol. 28, 2014, pp. 5696-5706.*
Shi, X. et al., "Quantitative Composition-Property Relationship of Aviation Hydrocarbon Fuel Based on Comprehensive Two-Dimensional Gas Chromatography with Mass Spectrometry and Flame Ionization Detector", Fuel, vol. 200, 2017, pp. 395-406.*

* cited by examiner

*Primary Examiner* — Daniel S Larkin
(74) *Attorney, Agent, or Firm* — Hartman Global IP Law; Gary M. Hartman; Domenica N. S. Hartman

(57) ABSTRACT

Methods for classification of hydrocarbon mixtures that include performing two-dimensional gas chromatography on a hydrocarbon mixture to obtain a chromatogram using a two-dimensional gas chromatograph equipped with a flame ionization detector, a reversed phase column configuration with a primary mid-polar or polar column and a secondary non-polar column, and a standard mixture. Classification is performed in which groups of hydrocarbons are identified and labeled based on peaks associated with the standard mixture, after which a quantification process is performed.

18 Claims, 20 Drawing Sheets
(20 of 20 Drawing Sheet(s) Filed in Color)

METHODS FOR CLASSIFICATION OF HYDROCARBON MIXTURES

CROSS-REFERENCE TO RELATED APPLICATIONS

This application claims the benefit of U.S. Provisional Application No. 62/751,331, filed Oct. 26, 2018, the contents of which are incorporated herein by reference.

BACKGROUND OF THE INVENTION

The present invention generally relates to gas chromatography. The invention particularly relates to methods of classification of hydrocarbon mixtures analyzed with a two-dimensional gas chromatography, and the ability to do so without requiring the use of mass spectrometry.

Comprehensive two-dimensional gas chromatography (GC×GC) has received considerable attention in many research fields, including fuel analysis. GC×GC has two separate columns, commonly designated as primary and secondary columns, each with two individual stationary phases. A modulator is utilized to inject the effluent from the primary (first dimension) column into the secondary (second dimension) column. In setups with the primary column containing a non-polar stationary phase and the secondary column containing a polar stationary phase, the column configuration is referred to as a normal phase. Alternatively, when the primary column contains a polar stationary phase and secondary column contains a non-polar stationary phase, the column configuration is referred to as a reversed phase. Hydrocarbon compounds separated in the secondary column consecutively enter a detector, the output of which yields a retention plane of the first-dimension separation by second-dimension separation.

Currently, GC×GC systems equipped with a time-of-flight mass spectrometer (TOF/MS, or TOFMS) and a flame ionization detector (FID) are state-of-the-art instruments for, respectively, qualitative and quantitative analysis of complex fuel mixtures (as nonlimiting examples, aviation and diesel fuels). Time-of-flight mass spectrometers comprises a mass analyzer and a detector that obtain qualitative data, but not quantitative data. An ideal system has both TOF/MS and FID detectors on the same instrument. However, TOF/MS is considerably more expensive than systems that only include FID. Therefore, many laboratories are financially limited to GC×GC systems without a mass spectrometer. However, FID does not provide any identification to the peaks, and therefore further classification is necessary. Classification as used herein is the process of grouping hydrocarbons into groups with the same carbon number from the same hydrocarbon class. Currently, the classification process is typically completed by an analyst. After the classification is completed, the quantification follows by summing the peak areas of the hydrocarbon compounds in each group. Consecutively, the weight percent of each group is calculated by dividing the total peak area of the group by the total peak area of the sample.

In view of the above, it can be appreciated that it would be desirable if systems and/or methods were available that were capable of performing classification without relying on an analyst and without the use of mass spectrometry.

BRIEF DESCRIPTION OF THE INVENTION

The present invention provides methods capable of obtaining a detailed chemical analysis of hydrocarbon mixtures via automated classification and quantification processes and without requiring the use of mass spectrometry.

According to one aspect of the invention, a method is provided that includes performing two-dimensional gas chromatography on a hydrocarbon mixture to obtain a chromatogram displaying peaks associated with hydrocarbons within the hydrocarbon mixture using a two-dimensional gas chromatograph (GC×GC) equipped with a flame ionization detector (FID), a reversed phase column configuration with a primary mid-polar or polar column and a secondary non-polar column, and a standard mixture. A classification process is then performed using gas chromatography imaging and data processing software, to group the hydrocarbons displayed in the chromatogram into groups with the same carbon number from the same hydrocarbon class, wherein the groups are identified and labeled based on hydrocarbon peaks associated with the standard mixture. A quantification process is then performed that includes summing the peak areas of the hydrocarbons in each group classified in the chromatogram to determine a total peak area of each group and then calculating the weight percent of each group by dividing the total peak area of the group by the total peak area of the hydrocarbon mixture.

Technical effects of the method described above preferably include the ability to perform classification on complex hydrocarbon mixtures, including but not limited to aviation and diesel fuels, without relying on an analyst to perform the classification step and without the use of mass spectrometry.

Other aspects and advantages of this invention will be appreciated from the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Methods described herein are capable of providing reversed phase classification of hydrocarbon mixtures (petroleum and non-petroleum based) with carbon numbers in a range of C6 through C33 using a comprehensive two-dimensional gas chromatography (GC×GC) system equipped with a flame ionization detector (FID). These systems and methods can obtain a detailed chemical analysis via an automated classification step using only twenty-four standard hydrocarbon compounds without the need of a GC×GC system equipped with a mass spectrometer. Systems suitable for use with such methods preferably include a gas chromatograph with a split injection system equipped with a capillary injection port with a deactivated glass liner, a flame ionization detector, two-stage thermal modulation system, and a cryo auto-fill unit.

Figure 5:
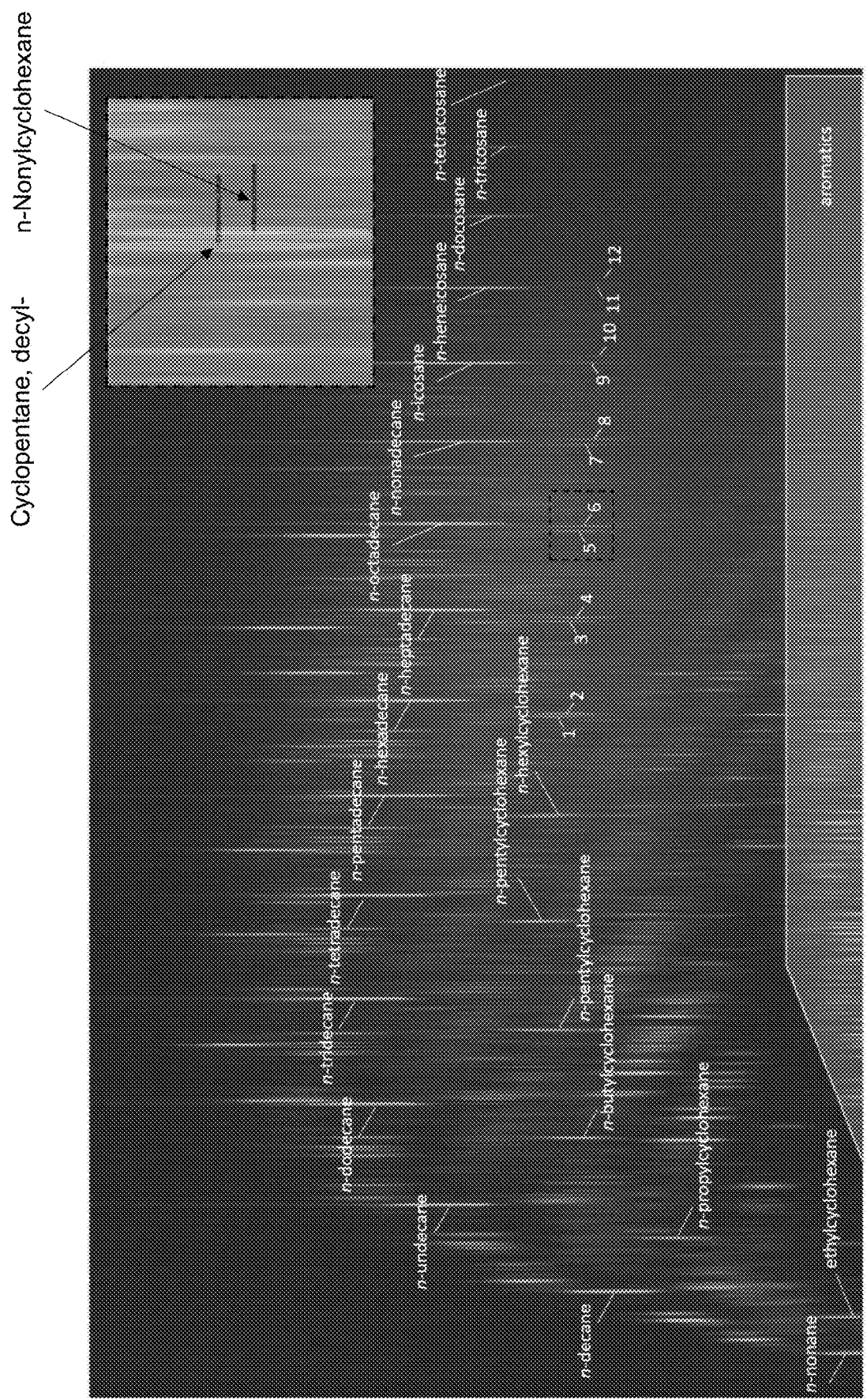
FIG. 5 shows a magnified portion of a GC×GC-TOF/MS chromatogram (m/z range of 45 to 550) indicating the monocycloparaffin landmark peaks in the diesel fuel sample. The numbers on the chromatogram referred to (1) n-octylcyclopentane, (2) n-heptylcyclohexane, (3) n-nonylcyclopentane, (4) n-octylcyclohexane, (5) n-decylcyclopentane, (6) n-nonylcyclohexane, (7) n-undecylcyclopentane, (8) n-decylcyclohexane, (9) n-dodecylcyclopentane, (10) n-undecylcyclohexane, (11) n-tridecylcyclopentane, and (12) n-dodecylcyclohexane.
Figure 6:
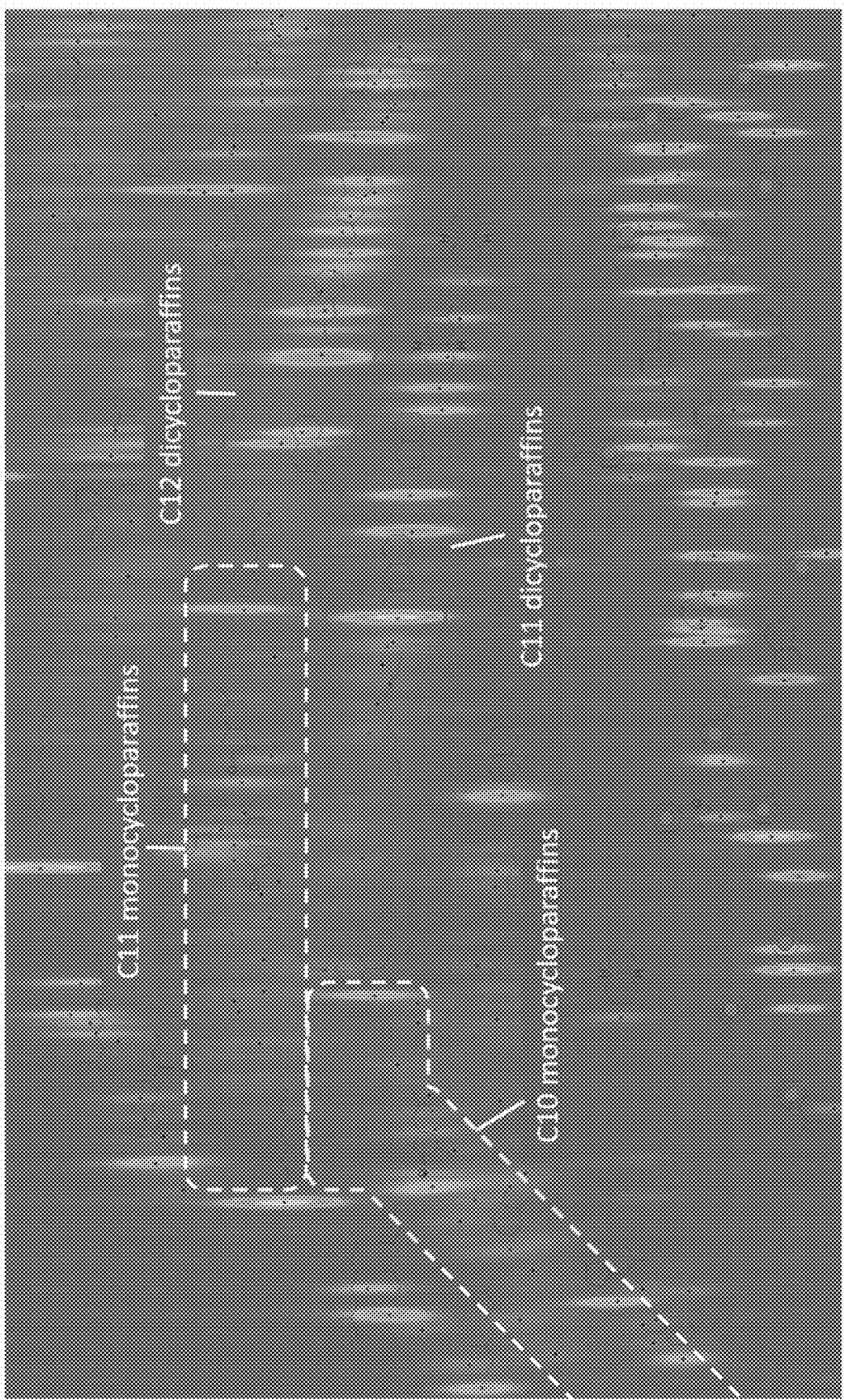
FIG. 6 shows a magnified portion of a GC×GC-TOF/MS chromatogram (m/z range of 45 to 550) indicating the elution order of mono- and dicycloparaffins in a diesel fuel sample.

Nonlimiting embodiments of the invention will now be described in reference to experimental investigations leading up to the invention. The investigations utilized two samples, a first of which was a commercially available petroleum-based diesel fuel, though any middle distillate reference material with a wide boiling range and a broad range of all hydrocarbon class constituents could have been utilized, including but not limited to aviation fuels such as jet fuels. The second sample was composed of the following twenty-four standard hydrocarbon compounds: n-octane (1), CAS #: 111-65-9, n-dodecane (2), CAS #: 112-40-3, n-hexadecane (3), CAS #: 544-76-3, perhydrophenalene (4), CAS #: 2935-07-1, tetradecahydroanthracene (5), CAS #: 6596-35-6, toluene (6), CAS #: 108-88-3, ethylbenzene (7), CAS #: 100-41-4, n-propylbenzene (8), CAS #: 103-65-1, n-butylbenzene (9), CAS #: 104-51-8, n-hexylbenzene (10), CAS #: 1077-16-3, indan (11), CAS #: 496-11-7, 4,7-dimethylindan (12), CAS #: 6682-71-9, 1,1-dimethyltetralin (13), CAS #: 1985-59-7, 1,1,6-trimethyltetralin (14), CAS #: 475-03-6, naphthalene (15), CAS #: 91-20-3, 2-methylnaphthalene (16), CAS #: 91-57-6, 1,8-dimethylnaphthalene (17), CAS #: 569-41-5, biphenyl (18), CAS #: 92-52-4, 4-methylbiphenyl (19), CAS #: 644-08-6, 4,4-dimethylbiphenyl (20), CAS #: 613-33-2, phenanthrene (21), CAS #: 85-01-8, 1-methylanthracene (22), CAS #: 610-48-0, pyrene (23), CAS #: 129-00-0, and 1-methylpyrene (24), CAS #: 2381-21-7. The purity of all standards was at least the HPLC grade purity. The numbers in parentheses refer to FIG. 5. n-Pentane and dichloromethane (DCM) were used as solvents. Acetone was used for syringe wash.

Equipment used for the investigations included an Agilent 7890B gas chromatograph (GC) with an FID, a thermal modulator (commercially available from the LECO Corporation), an Agilent 7683B series injector, and an HP 7683 series autosampler. ChromaTOF® software optimized for GC×GC-FID (LECO Corporation) was used for gas chromatography imaging and data processing, and classification development. LECO Pegasus GC-HRT 4D (EI) High-Resolution TOF/MS (LECO Corporation) with an Agilent 7890B gas chromatograph, a thermal modulator cooled with liquid nitrogen, and an Agilent G4513A auto-injector was used for qualitative analysis of the samples. ChromaTOF® was utilized for data collection (with an m/z of 45 to 550), processing, and analysis. Identification of the hydrocarbon compounds was achieved by matching the measured mass spectra (similarity value of greater than 800) with Wiley (2011) and NIST (2011) mass spectral databases. GC×GC-TOF/MS was used for validation purposes.

In the reversed phase column configuration, the polarity of the primary column can have different phases (polar or mid-polar) while the secondary column always has a non-polar phase. The methods described herein were developed and validated for both phases, that is, polar (polyethylene glycol) and mid-polar ((50%-Phenyl)-methylpoly-siloxane). The primary column length was 30 or 60 meters with a 0.25 mm internal diameter (ID), and was internally coated to a film thickness of 0.25 µm. Commercially available polar columns of this type include VF-WAXms (Agilent), Stabilwax (Restek), Rtx-WAX (Restek), and CB-WAX (Agilent). Commercially available mid-polar columns of this type include DB-17 ms (Agilent), Rxi-17Sil MS (Restek), Rtx-50 (Restek), and BPX-50 (Trajan). The secondary non-polar column (dimethyl polysiloxane) can have a length of 0.8 to 1.2 m, with a 0.10 or 0.25 mm ID, and internally coated to a film thickness of 0.10 or 0.25 µm. It should be noted here that the secondary column length has to be adjusted in order to avoid wrap-around effect. Commercially available non-polar columns of this type include Rxi-1ms (Restek) and DB-1 (Agilent).

Figure 11:
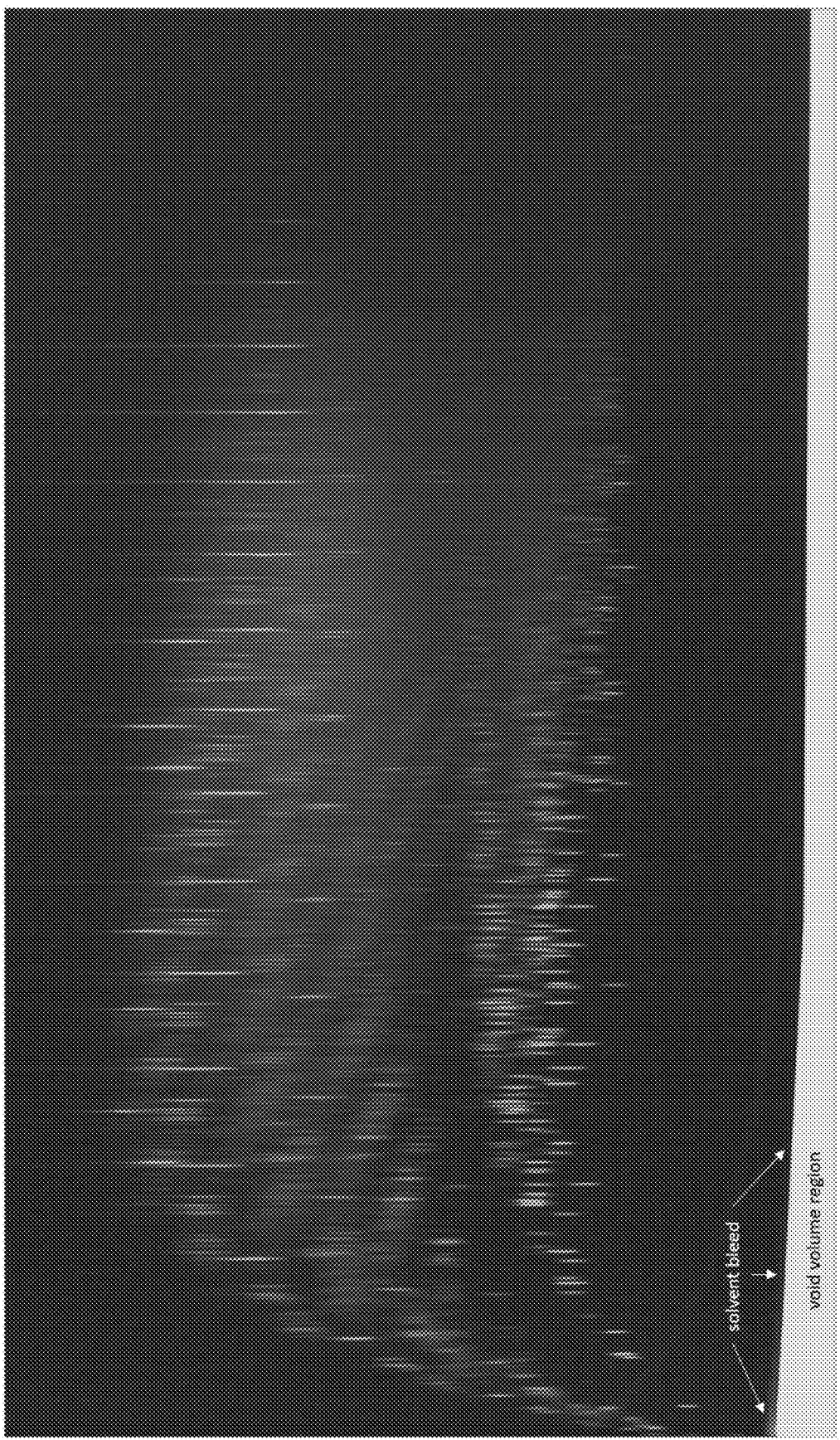
FIG. 11 shows a GC×GC-TOF/MS chromatogram of a diesel fuel sample (m/z range of 45 to 550) indicating solvent bleed and secondary column void volume region.

Optimization of separation in the selected GC×GC instrument will depend on the application and therefore will not be discussed in any detail herein. All chromatograms referenced herein were recorded using DB-17 ms as the primary and DB-1 as the secondary column. The detailed parameters of the method used, GC×GC linearity, and repeatability are described in published paper Vozka P., Mo H., Simacek P., Kilaz G., Middle distillates hydrogen content via GC×GC- FID, Talanta 2018; 186:140-6, the contents of which are incorporated herein by reference. A S/N value of 50 was used for data processing. For the methods disclosed herein, wrap-around is acceptable unless it is not a total wrap-around, namely, peaks can elute in void volume region (FIG. 11). If total wrap-around is present, one may trim the secondary column or increase the secondary oven temperature offset.

For sample preparation, the middle distillate reference sample was prepared by diluting 10 µl of diesel fuel sample in 1 ml of solvent in a 2 ml autosampler vial. DCM was used as a solvent for the mid-polar columns and n-pentane was used for the polar primary column. A standard mixture of hydrocarbon compounds (hereinafter, "standard mixture") was prepared by placing the liquid scintillation vial on an analytical balance, adding about 5 mg (several crystals) of each solid standard compound, adding about 5 mg (about one drop) of each liquid standard compound, and then filling the liquid scintillation vial with about 15 ml of the solvent.

Figure 1:
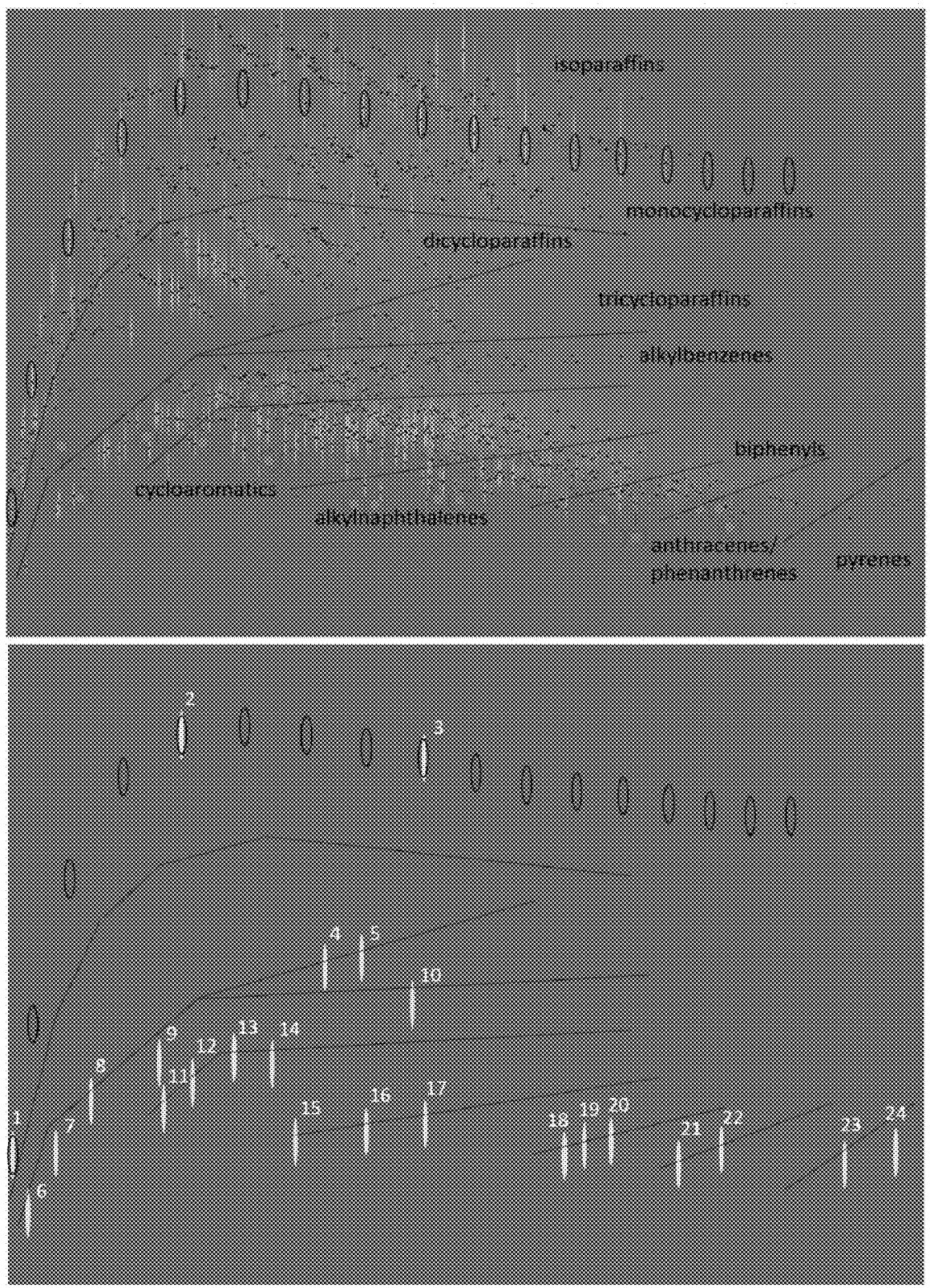
FIG. 1 shows a GC×GC-TOF/MS chromatogram of a diesel fuel sample (m/z range of 45 to 550) indicating the main hydrocarbon classes (left) and representation of a standard mixture with the position of all eluted peaks (right).

For classification, carbon number increases with the increasing primary retention time in every hydrocarbon class (i.e., from the left side of the chromatogram to the right side). The complete chromatogram of the diesel sample without the classification borders is shown in FIG. 11. The complete chromatogram of the diesel sample with main hydrocarbon regions obtained from GC×GC-TOF/MS is shown in FIG. 1.

Figure 10:
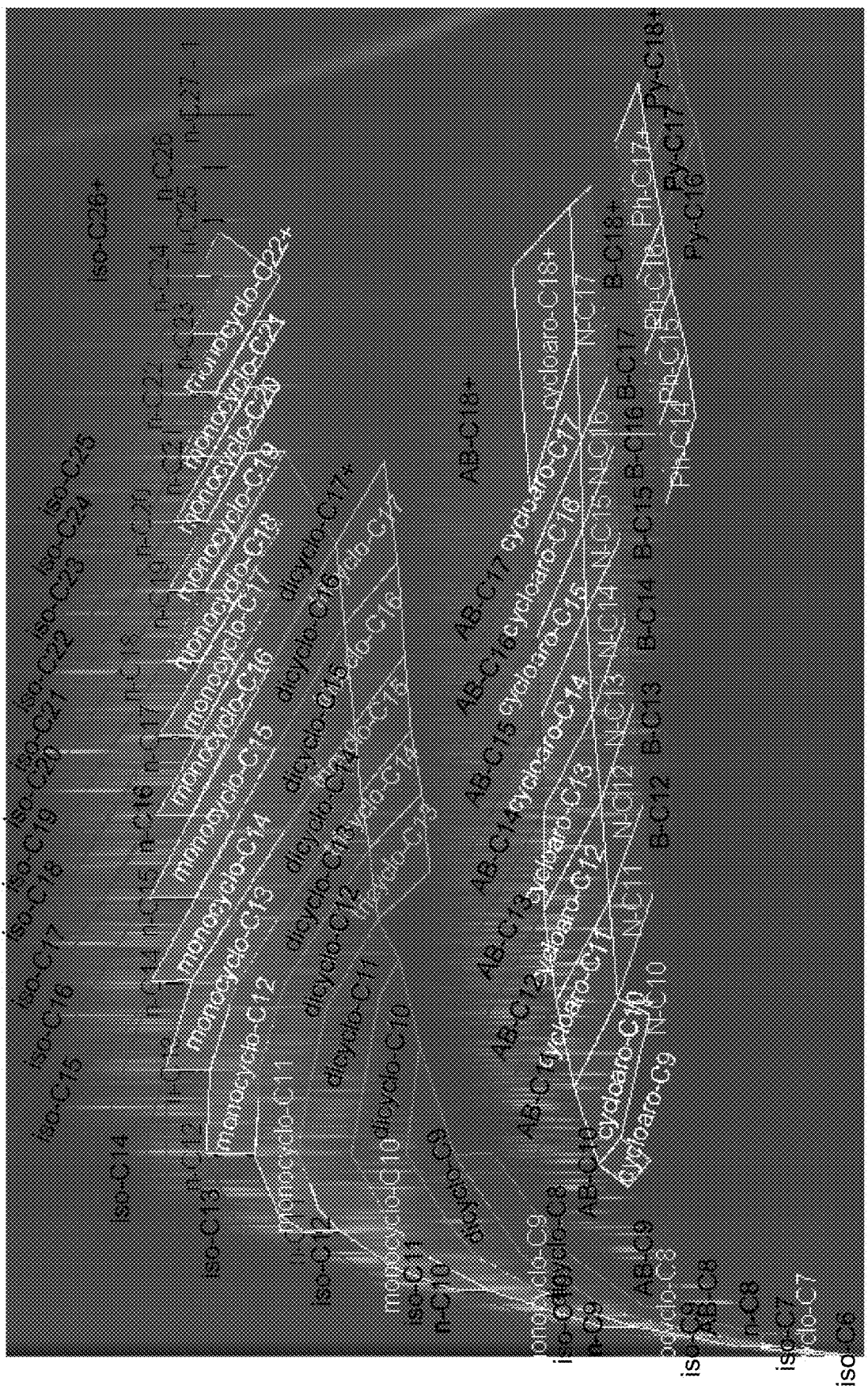
FIG. 10 shows a GC×GC-FID chromatogram of a diesel fuel sample with hydrocarbons grouped based on carbon number.

The following paragraphs detail steps in a nonlimiting classification method for identifying hydrocarbons in chromatograms obtained with GC×GC-FID. FIG. 10 shows the classification after completion with a boarder identifying the hydrocarbon groups.

Figure 2:
FIG. 2 shows a GC×GC-FID chromatogram of a diesel fuel sample with the peaks associated with n-octane, n-dodecane, and n-hexadecane labeled.
Figure 3:
FIG. 3 shows the chromatogram of FIG. 2 after adjusting the colors.
Figure 4:
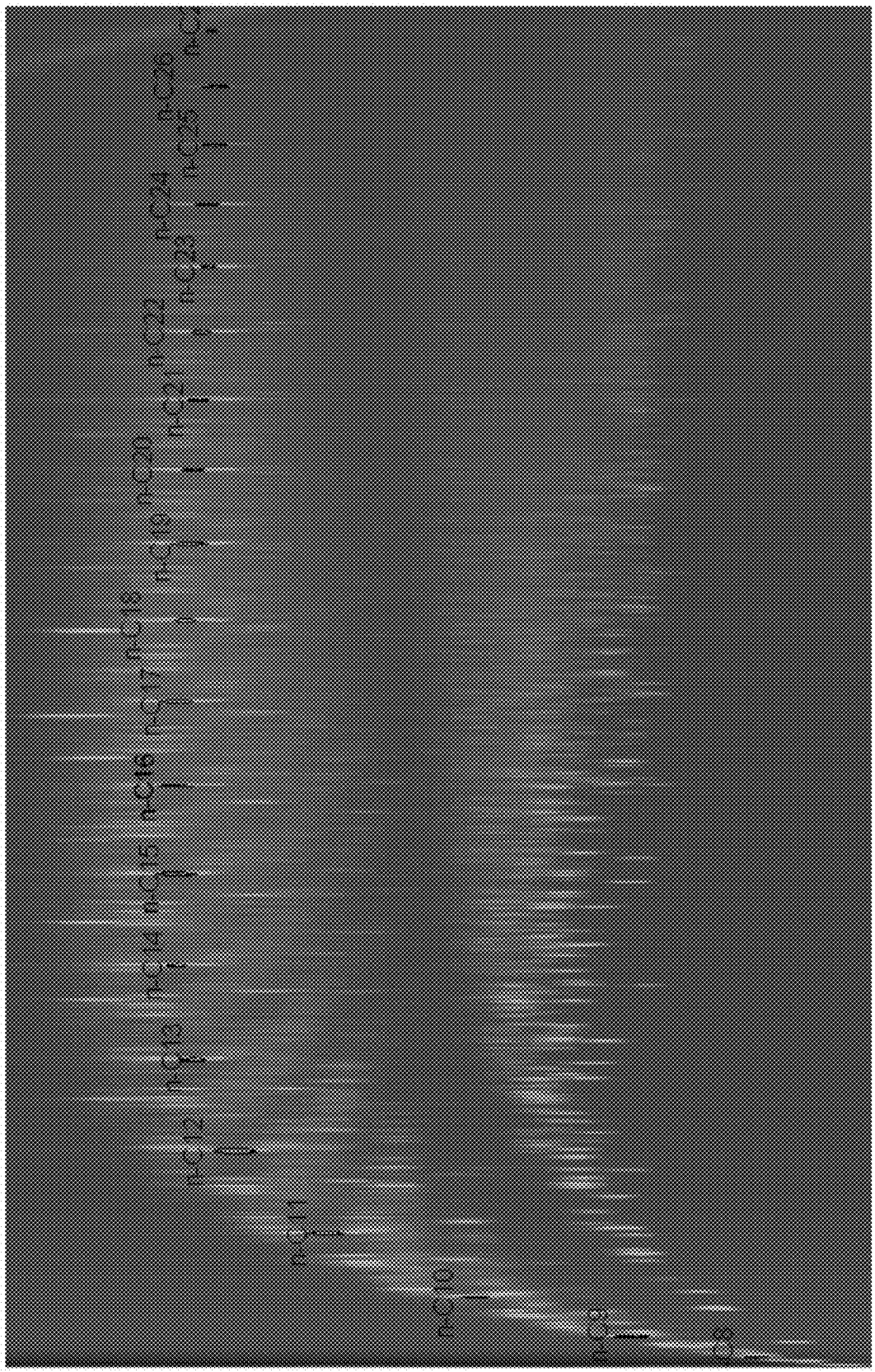
FIG. 4 shows a GC×GC-FID chromatogram of a diesel fuel sample with the locations of all n-paraffin regions (–) labeled.

To identify n-paraffins, the standard mixture was opened as a background in the ChromaTOF® software. The first compound (from the left) in the n-paraffin region was n-octane, the second one was n-dodecane, and the third one was n-hexadecane. Borders were drawn for these three n-paraffins. Then the diesel sample was opened as the background. FIG. 2 represents what was displayed onscreen at this point in the process. The chromatogram colors were adjusted so just the most abundant compounds are visible (these were mostly n-paraffins) as shown in FIG. 3. Specifically, the colors were set from 0% to 100% with the ratio of 0.6 to 0.8. Based on three n-paraffin standards, the classification was completed for the rest of the n-paraffins. FIG. 4 displays n-paraffins eluting in a very clear order with the increasing carbon number from the left of the chromatogram to the right, which promotes ease of identification. When all n-paraffins were identified and labeled, the classification appeared as shown in FIG. 4.

Figure 12:
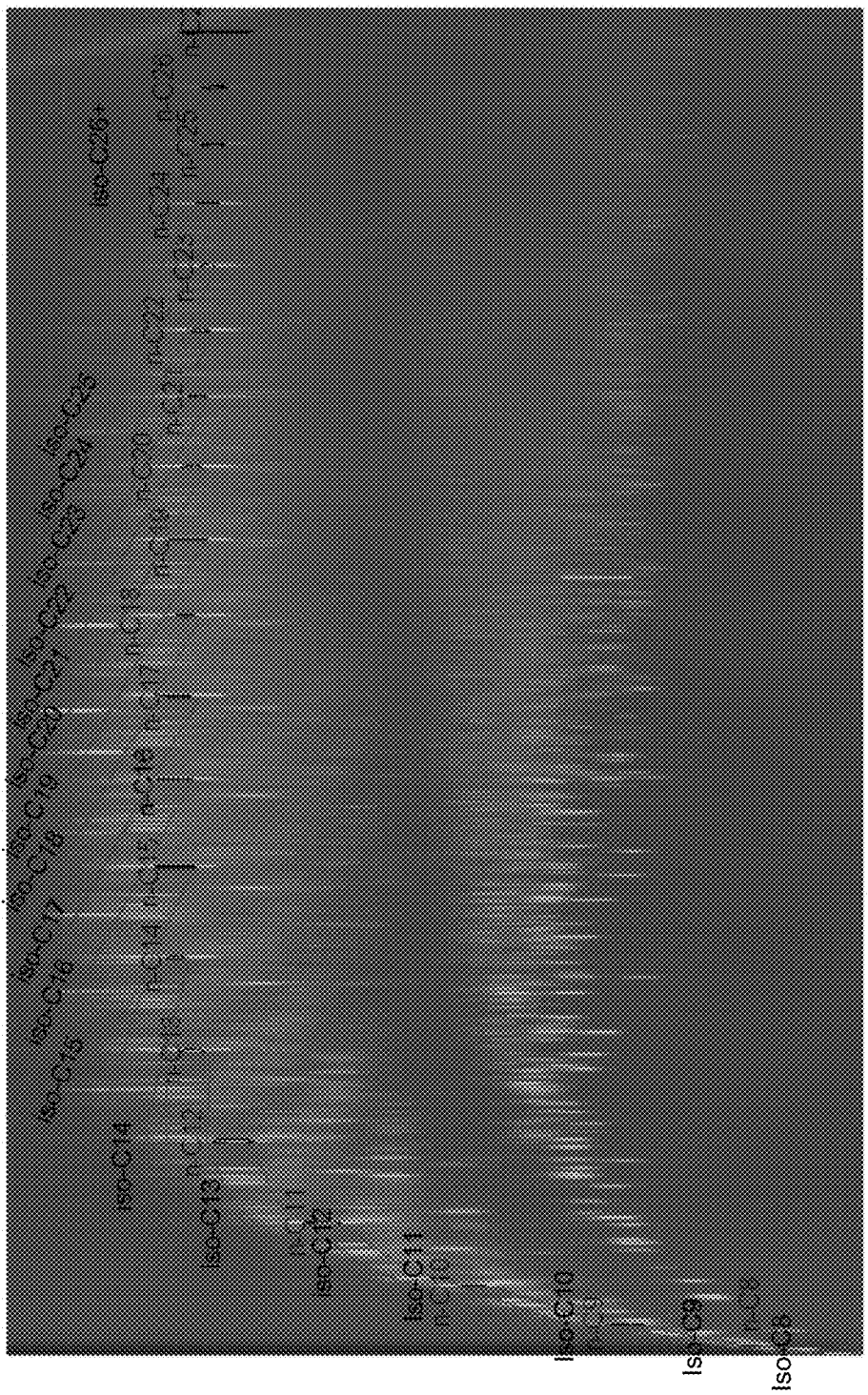
FIG. 12 shows a GC×GC-FID chromatogram of a diesel fuel sample with the locations of all isoparaffin regions (iso-).

To identify isoparaffins, the diesel sample was opened as a background in ChromaTOF® software. The isoparaffins could be observed after adjusting the colors to the normal view (e.g., 0% to 100% with a ratio of 1.0 to 1.5). The borders were drawn for isoparaffins. No standards were necessary for drawing the isoparaffin borders. Isoparaffins eluted between and above the n-paraffins. Isoparaffins with the same carbon number eluted from the n-paraffin to the left. FIG. 12 represents the classification after this step. Cycloparaffins eluted between n-paraffins and aromatic compounds. In the middle distillate analyzed, mono-, di-, and tricycloparaffins were found.

Figure 13:
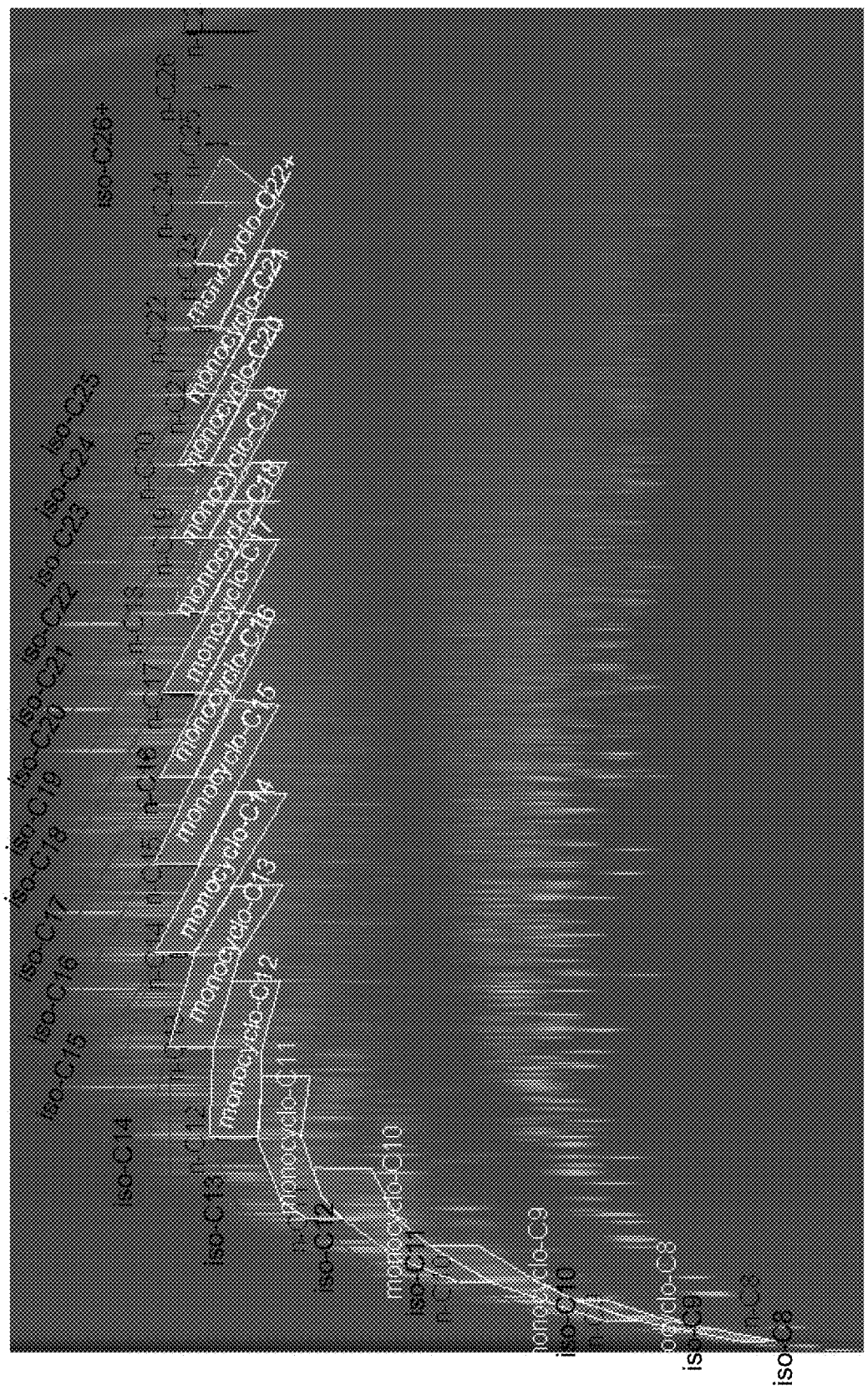
FIG. 13 shows a GC×GC-FID chromatogram of a diesel fuel sample with the locations of all monocycloparaffin regions (monocyclo-).

To identify monocycloparaffins, the diesel sample was opened as a background in ChromaTOF® software. The chromatogram colors were adjusted from 0% to 100% with a ratio of 0.6 to 0.8. The borders were drawn for monocycloparaffins. Monocycloparaffins eluted between n-paraffins and dicycloparaffins. The borders between mono- and dicycloparaffins were well defined by n-alkyl cyclohexanes, which could be viewed on the chromatogram following the path of n-paraffins, as shown in the GC×GC-TOF/MS chromatogram of FIG. 5. With increasing carbon number, two peaks close to each other can be observed. The left peak was alkyl-cyclopentane and the right peak was alkyl-cyclohexane. All of the peaks between n-paraffin and alkyl-cyclopentane were alkyl-methylcyclohexanes. At lower carbon numbers these two peaks might be very close to each other or might even coelute. However, all these peaks belong to the monocycloparaffins group. The borders of the n-paraffins and the monocycloparaffins of the same carbon number should intercept. FIG. 13 shows the classification after this step was completed.

Figure 14:
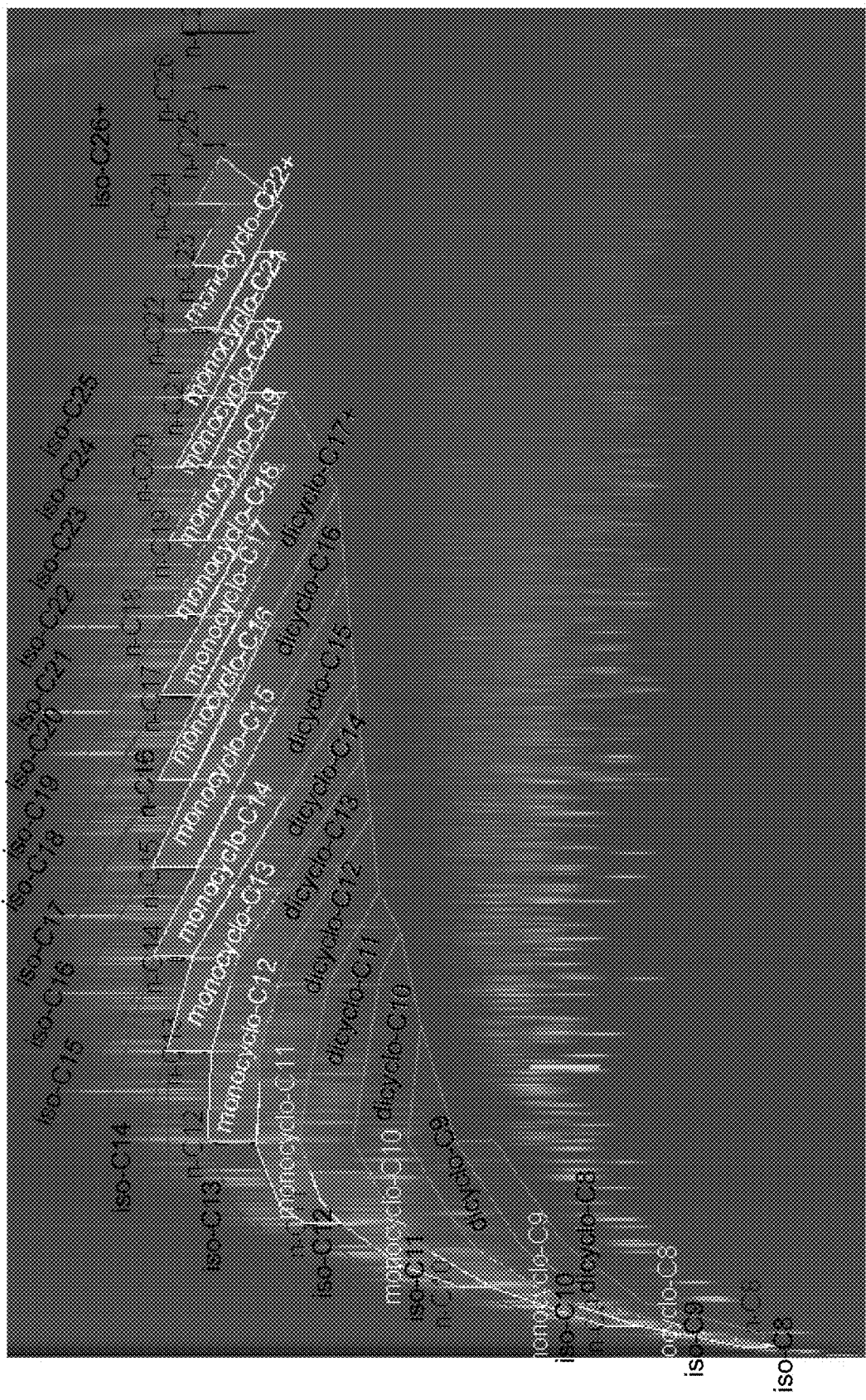
FIG. 14 shows a GC×GC-FID chromatogram of a diesel fuel sample with the locations of all dicycloparaffin regions (dicyclo-).

To identify dicycloparaffins, the diesel sample was opened as a background in the ChromaTOF® software. The colors were adjusted to the normal view (e.g., from 0% to 100% with a ratio of 1.0 to 1.5). The borders were found between dicycloparaffins and tricycloparaffins. The beginning of tricycloparaffins was the end of dicycloparaffins. The borders for dicycloparaffins were drawn which eluted between the monocycloparaffins and the tricycloparaffins. Dicycloparaffin borders were directly connected to monocycloparaffins; however, the carbon number of dicycloparaffins is one carbon number higher than that of monocycloparaffins. Dicloparaffins start with carbon number 8. FIG. 14 shows the classification after this step was completed.

Figure 7:
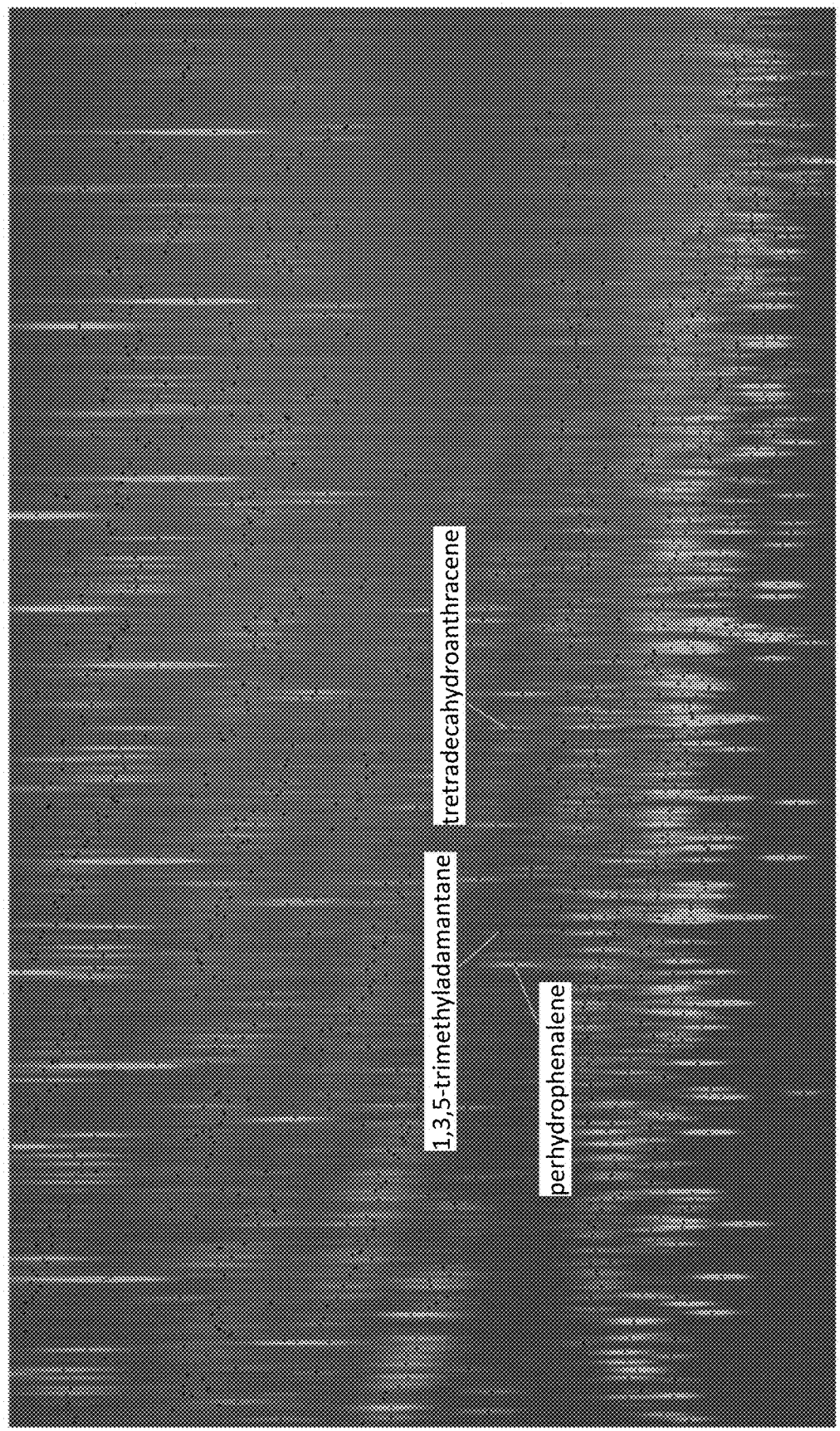
FIG. 7 shows a GC×GC-TOF/MS chromatogram of a diesel fuel sample (m/z range of 45 to 550) with the location of tricycloparaffin region identified.
Figure 15:
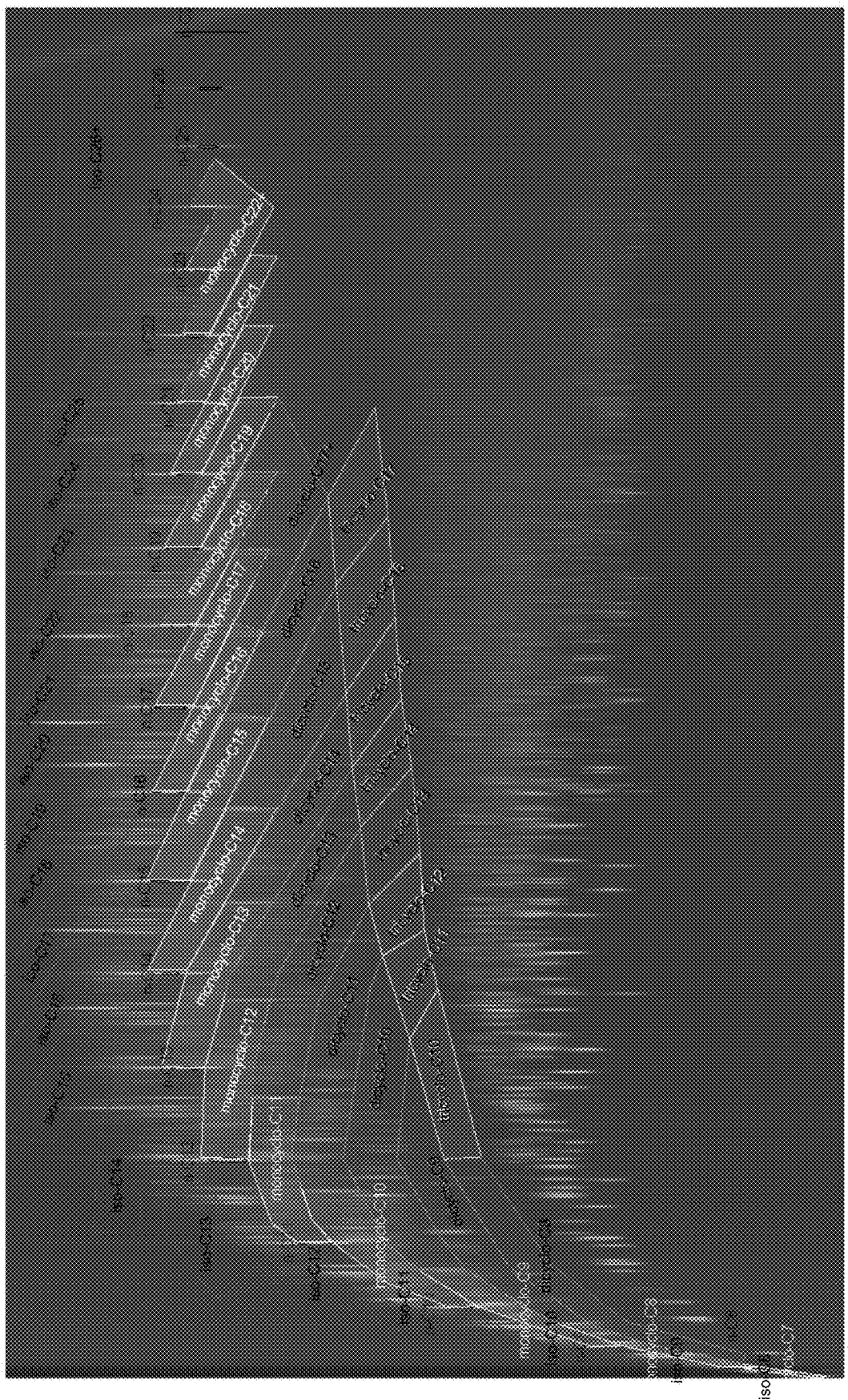
FIG. 15 shows a GC×GC-FID chromatogram of diesel fuel sample with the locations of all tricycloparaffin regions (tricyclo-).

To identify tricycloparaffins, the standard mixture was opened as a background in the ChromaTOF® software. The first compound from the left in the tricycloparaffins region was perhydrophenalene and the second one was tetradecahydroanthracene. These tricycloparaffin peaks eluted at the border between di- and tricycloparaffins. Therefore, these peaks served as the visual landmarks for drawing the border between di- and tricycloparaffins. FIG. 7 shows a GC×GC-TOF/MS chromatogram with a designated tricycloparaffin region. The diesel sample was opened as a background in the ChromaTOF® software with the normal view. The borders for tricycloparaffins were drawn, which eluted between the dicycloparaffins and the aromatics. Tricycloparaffin borders were directly connected to dicycloparaffins. However, the carbon number of tricycloparaffins is one carbon number higher than that of dicycloparaffins. Tricloparaffins start with carbon number 10. FIG. 15 shows the classification after this step was completed.

The next step was to identify aromatics. In reversed phase column configuration, the primary column can have either a polar or mid-polar phase. Columns with polar phase allow for better separation between aromatic compound classes, though the operating temperature range is very limited. Therefore, the classifications for aromatics using both phases are discussed. For jet fuel, aromatics are basically divided into four hydrocarbon classes, that is, alkylbenzenes, cycloaromatics (i.e., naphthene-containing aromatic compounds such as indans, tetralins, and their alkyl-isomers), naphthalenes, and biphenyls. For diesel fuels, aromatics can contain additional classes with three fused benzene rings (anthracenes and phenanthrenes) and four fused benzene rings (pyrenes). The methods described herein were developed and validated for both types of primary columns (polar and mid-polar). However, if the polar primary column (e.g., VF-WAXms) was used, the borders between aromatic classes were easier to distinguish than the case where the mid-polar column was used.

Figure 8:
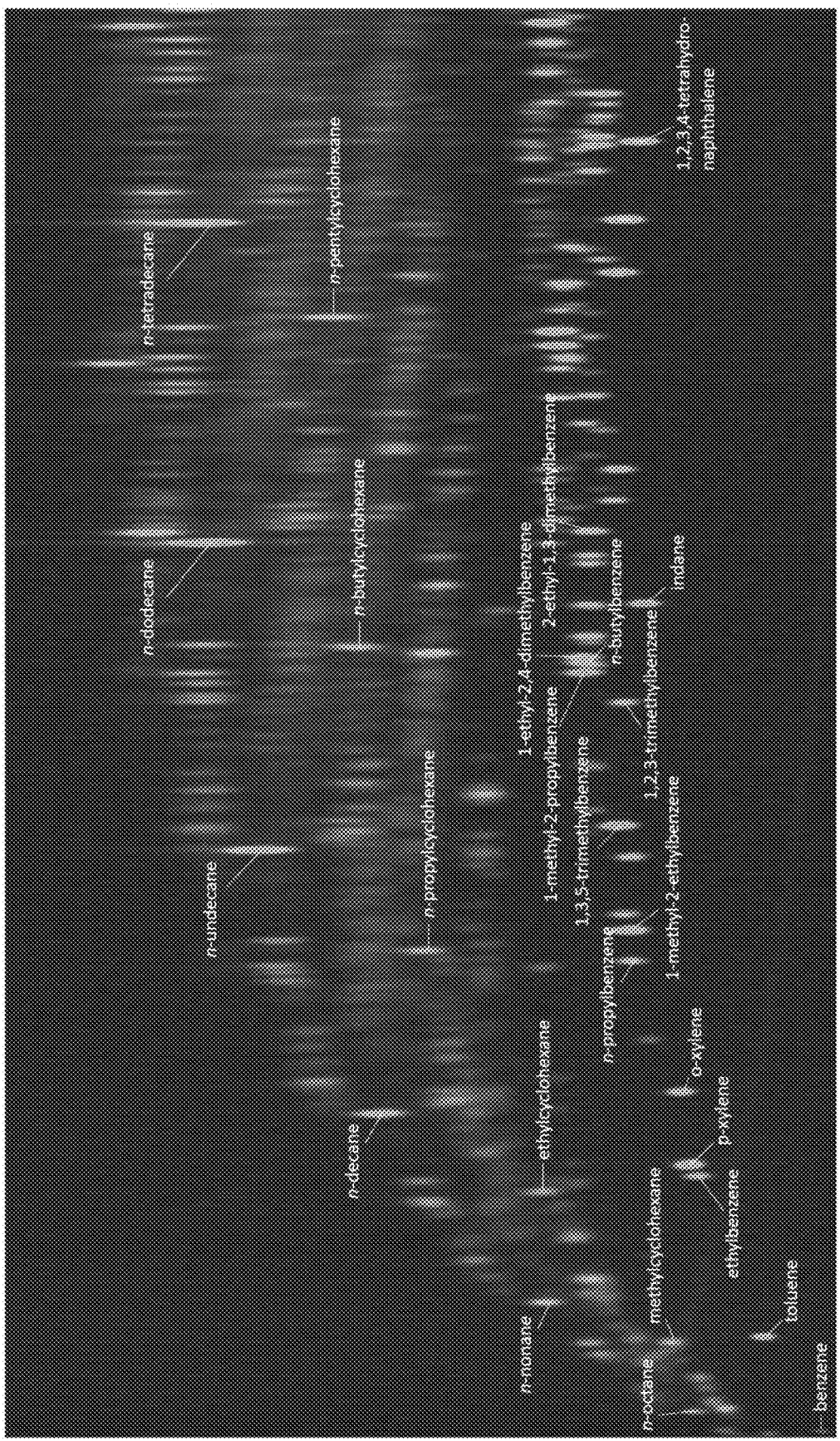
FIG. 8 shows a magnified portion of a GC×GC-TOF/MS chromatogram (m/z range of 45 to 550) indicating the aromatic landmark peaks in a diesel fuel sample.
Figure 16:
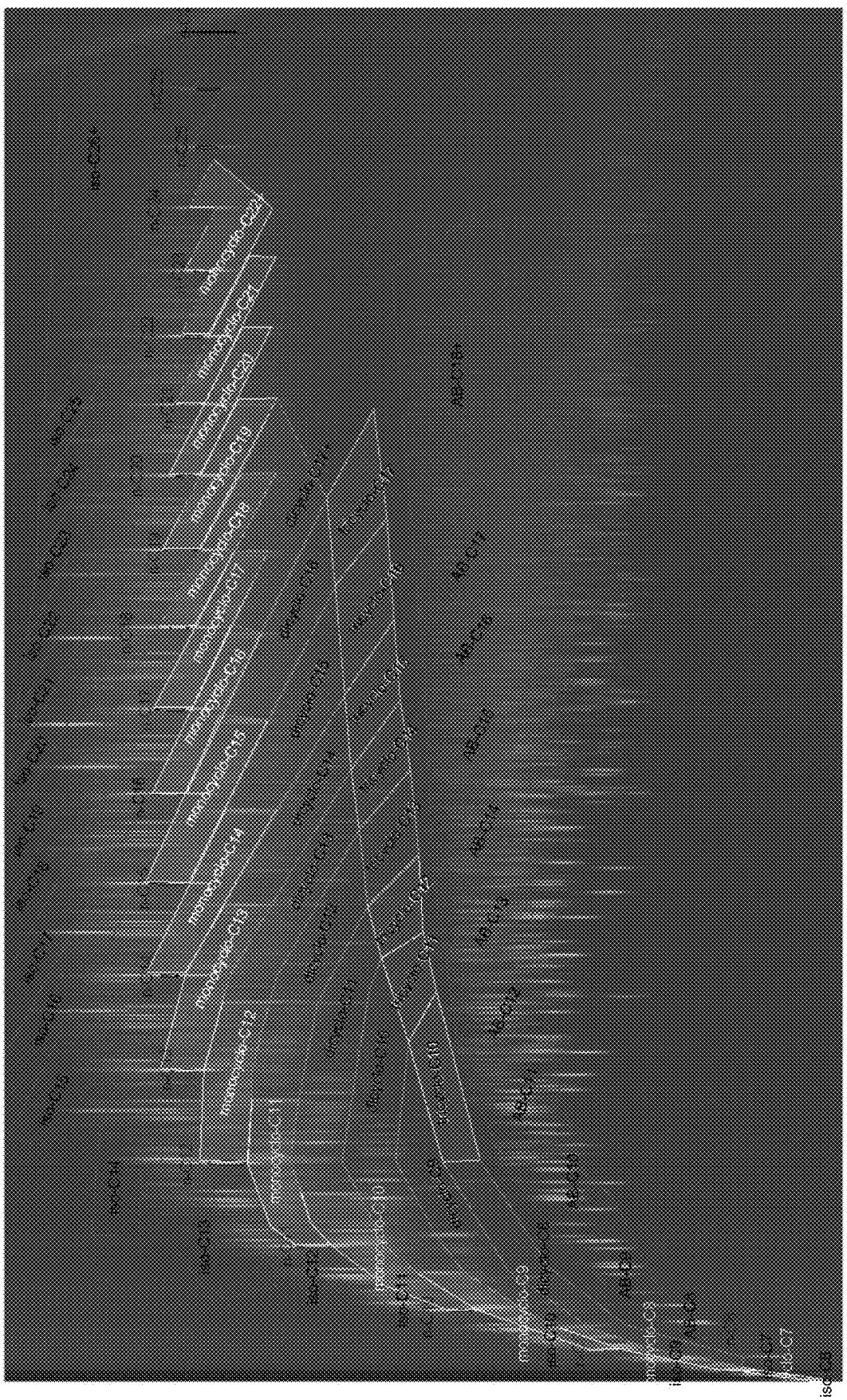
FIG. 16 shows a GC×GC-FID chromatogram of diesel fuel sample with the locations of all alkylbenzene regions (AB-).

For alkylbenzenes, the standard mixture was opened as a background in the ChromaTOF® software. The compounds in the alkylbenzene region from the left eluted in the following order: toluene, ethylbenzene, n-propylbenzene, n-butylbenzene, and n-hexylbenzene. The peaks corresponding to these compounds were marked as standards. The diesel sample was opened as the background. The above-mentioned standards and FIG. 8 were used to draw the borders for alkylbenzenes. The first four alkylbenzene compounds were used to help orient at the beginning of the alkylbenzene group. n-Hexylbenzene served as a landmark for higher carbon numbers. Alkylbenzenes eluted between saturates and cycloaromatics. The first compound in this group was benzene (served as a landmark, shown in FIG. 8). FIG. 16 shows the classification after this step was completed.

Figure 17:
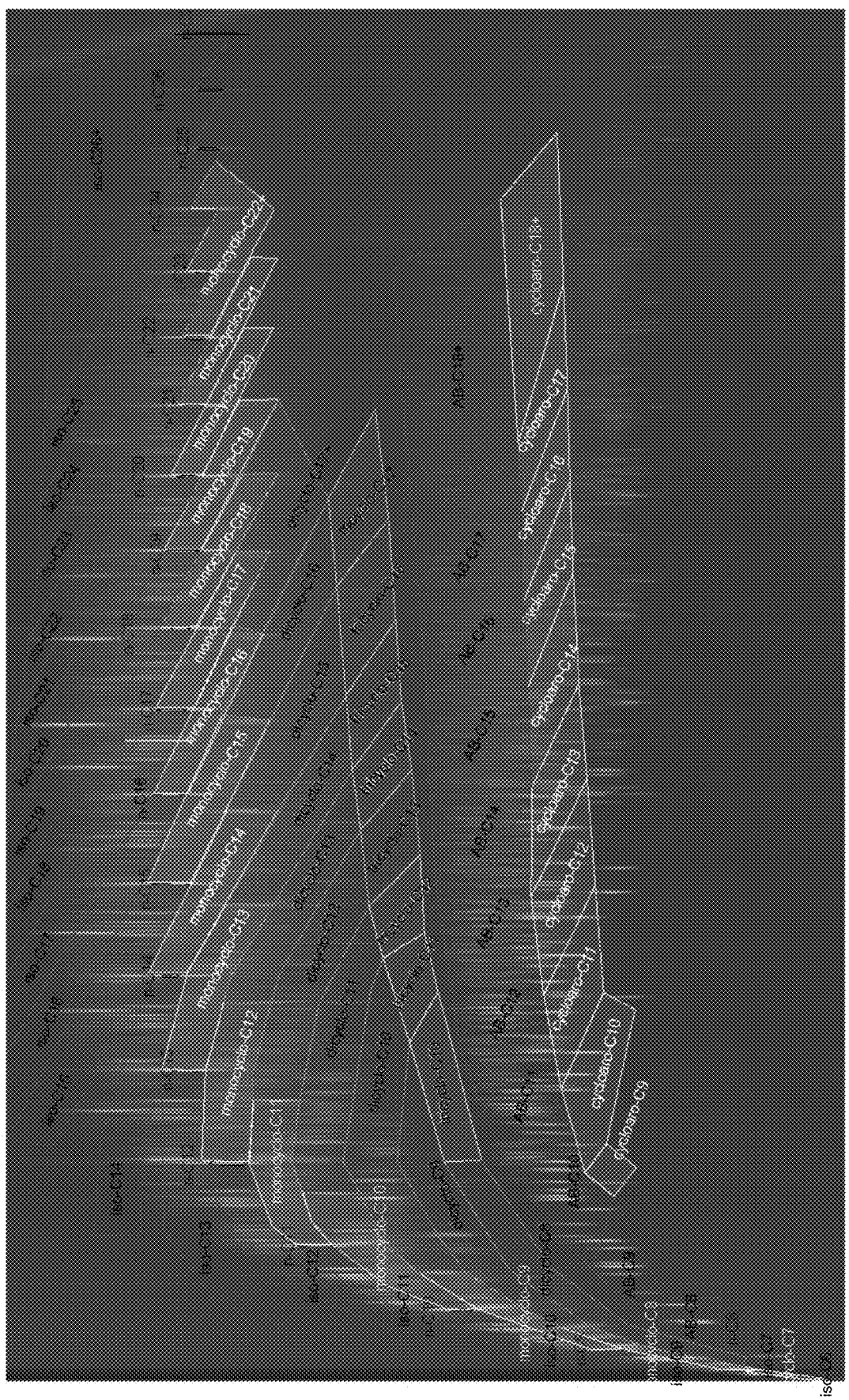
FIG. 17 shows a GC×GC-FID chromatogram of diesel fuel sample with the locations of all cycloaromatic regions (cycloaro-).

For cycloaromatics, the standard mixture was opened as a background in the ChromaTOF® software. The compounds in cycloaromatics region from the left eluted in the following order: indan, 4,7-dimethylindan, 1,1-dimethyltetralin, and 1,1,6-trimethyltetralin. The peaks corresponding to these compounds were marked as standards. These peaks served as landmarks for the beginning of cycloaromatic regions. The diesel sample was opened as the background. The above-mentioned standards were used to draw borders for cycloaromatics. Cycloaromatics eluted between alkylbenzenes and alkylnaphthalenes. The first cycloaromatic compound was indan (served as a landmark, shown in FIG. 8). Cycloaromatics and alkylbenzenes borders of the same carbon number were directly connected to each other. FIG. 17 shows the classification after this step was completed.

Figure 9:
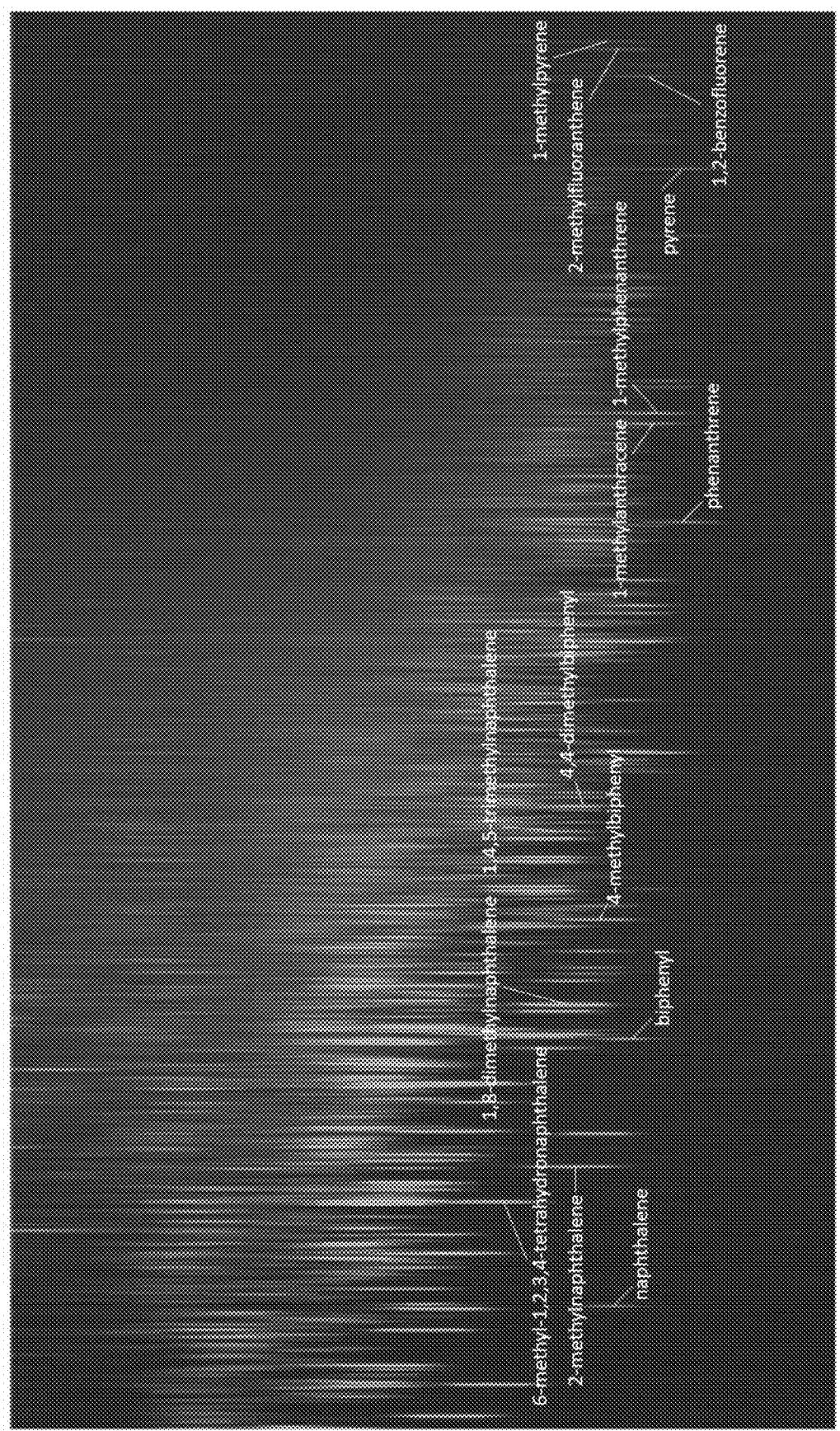
FIG. 9 shows a magnified portion of a GC×GC-TOF/MS chromatogram (m/z range of 45 to 550) indicating the aromatic landmark peaks in the diesel fuel sample.
Figure 18:
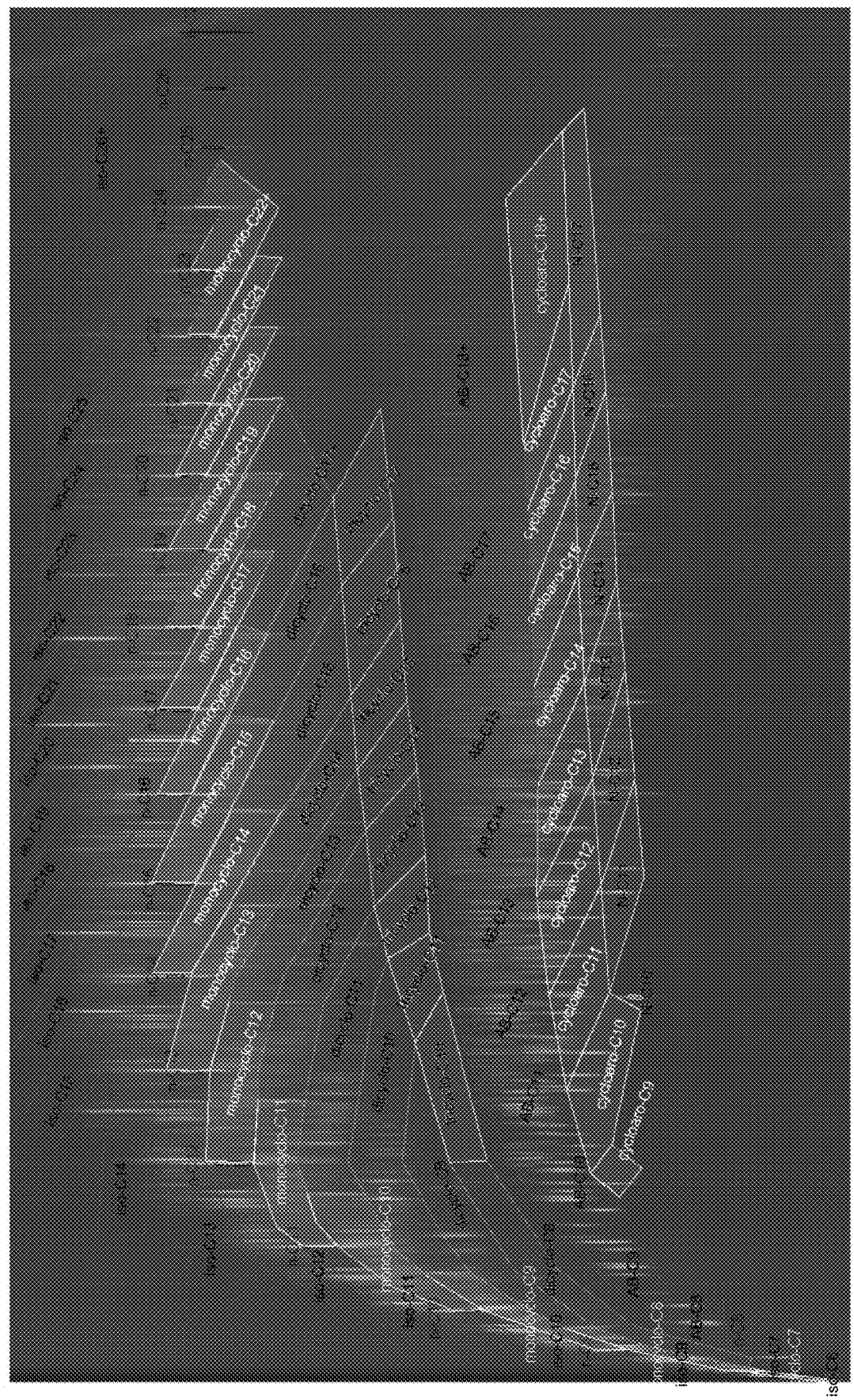
FIG. 18 shows a GC×GC-FID chromatogram of diesel fuel sample with the locations of all alkylnaphthalene regions (N-).

For alkynaphthalenes, the standard mixture was opened as a background in the ChromaTOF® software. The compounds in alkylnaphthalene region from the left eluted in the following order: naphthalene, 2-methylnaphthalene, and 1,8-di-methylnaphthalene. The peaks corresponding to these compounds were marked as standards. These peaks served as landmarks for the beginning of the alkylnaphthalene regions. The diesel sample was opened as the background. The above-mentioned standards and FIG. 9 were used to draw borders for the alkylnaphthalenes. Alkylnaphthalenes eluted between cycloaromatics and biphenyls. The first compound in this group was naphthalene (served as a landmark, shown in FIG. 9). The end of alkylnaphthalene region was defined by the beginning of the biphenyl region. Alkylnaphthalenes and cycloaromatics borders of the same carbon number were directly connected to each other. FIG. 18 shows the classification after this step was completed.

Figure 19:
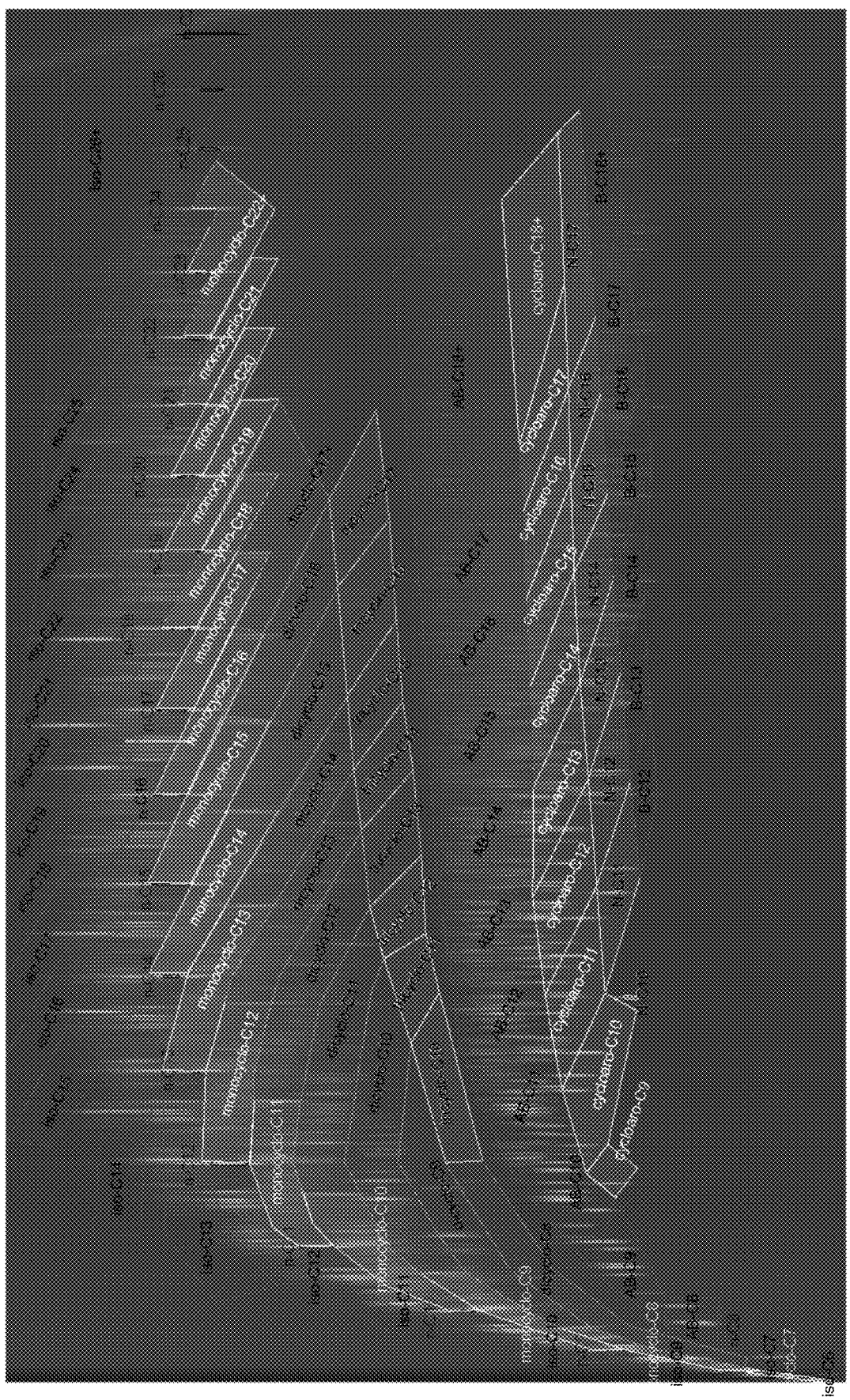
FIG. 19 shows a GC×GC-FID chromatogram of diesel fuel sample with the locations of all biphenyl regions (B-).

For biphenyls, the standard mixture was opened as a background in the ChromaTOF® software. The compounds in biphenyl region from the left eluted in the following order: biphenyl, 4-methylbiphenyl, and 4,4-dimethylbiphenyl. The peaks corresponding to these compounds were marked as standards. These peaks served as landmarks for the beginning of biphenyl regions. The diesel sample was opened as the background. The above-mentioned standards and FIG. 9 were used to draw borders for biphenyls. Biphenyls eluted between alkylbenzenes and anthracenes and phenanthrenes. The first compound in this group was biphenyl (served as a landmark, shown in FIG. 9). The end of biphenyl region was defined by the beginning of the anthracenes and phenanthrenes region. Biphenyl borders were directly connected to alkylnaphthalenes; however, the carbon number of biphenyls is one carbon number higher than that of alkylnaphthalenes. FIG. 19 shows the classification after this step was completed.

Figure 20:
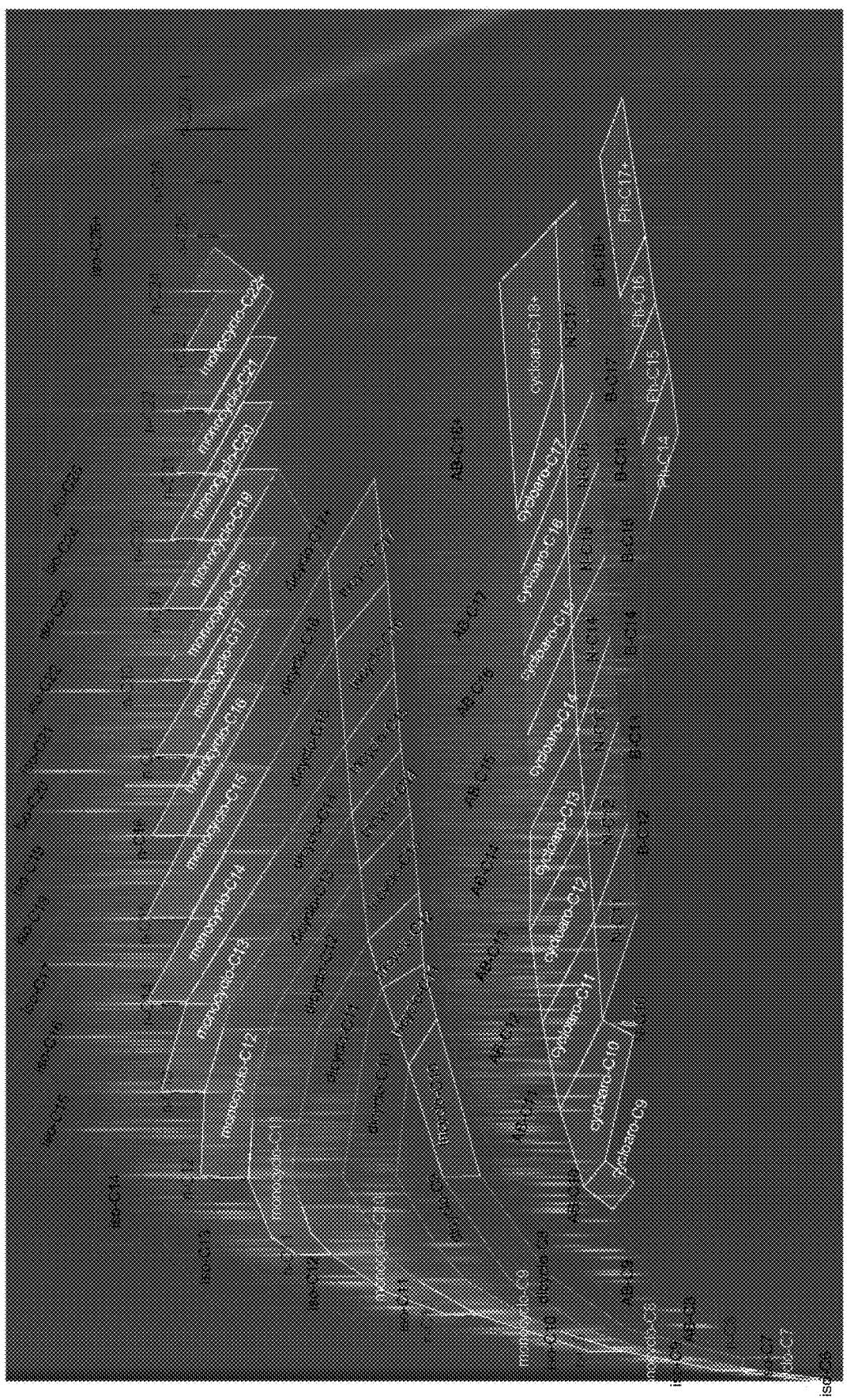
FIG. 20 shows a GC×GC-FID chromatogram of diesel fuel sample with the locations of all anthracene and phenanthrene regions (Ph-).

For anthracenes and phenanthrenes, the standard mixture was opened as a background in the ChromaTOF® software. The compounds in anthracene and phenanthrene region from the left eluted in the following order: phenanthrene and 1-methylanthracene. The peaks corresponding to these compounds were marked as standards. These peaks served as landmarks for the beginning of anthracene and phenanthrene regions. The diesel sample was opened as the background. The above-mentioned standards and FIG. 9 were used to draw borders for anthracenes and phenanthrenes. Anthracenes and phenanthrenes eluted between biphenyls and pyrenes. The first compound in this group was phenanthrene (served as a landmark, shown in FIG. 9). The end of anthracene and phenanthrene region was defined by the beginning of the pyrene region. Anthracene and phenanthrene borders were directly connected to biphenyls; however, the carbon number of anthracenes and phenanthrenes is one carbon number higher than that of biphenyls. FIG. 20 shows the classification after this step was completed.

For pyrenes, the standard mixture was opened as a background in the ChromaTOF® software. The compounds in pyrene region from the left eluted in the following order: pyrene and 1-methylpyrene. The peaks corresponding to these compounds were marked as standards. These peaks served as landmarks for the beginning of pyrene regions. The diesel sample was opened as the background. The above-mentioned standards and FIG. 9 were used to draw borders for pyrenes. Pyrenes eluted under anthracenes and phenanthrenes. The first compound in this group was pyrene (served as a landmark, shown in FIG. 9). Pyrenes borders and anthracene and phenanthrene borders of the same carbon number were directly connected to each other. FIG. 10 shows the classification after the borders were drawn.

Once the above-described classification was completed in the ChromaTOF® software (or any other gas chromatography imaging and data processing software, for example, GC Image™), the classification was included into a data processing method. Specifically, the sample of interest was processed, the recorded data was exported from the ChromaTOF® Peak Table into a spreadsheet software application (Microsoft Excel®), and all peak areas belonging to the same group and all peak areas belonging to the sample were summed. The response factors of all hydrocarbon compounds are equal to 1. Therefore, in order to obtain weight percentage (wt. %) for each group, the total peak area of the group was divided by the total peak area of the sample. Olefins were lumped with cycloparaffins and compounds containing heteroatoms were lumped with aromatics.

The above-described methods were validated by comparing the chromatogram outputs to those obtained from the GC×GC-TOF/MS. Additional methods utilized for further validation were GC-FID, ASTM D1319 and D6591, and a standard mixture of nineteen compounds.

While the invention has been described in terms of specific embodiments, it is apparent that other forms could be adopted by one skilled in the art. For example, the systems and methods could be used to identify various hydrocarbons in other mixtures, and materials and processes/methods other than those noted could be used. Therefore, the scope of the invention is to be limited only by the following claims.

The invention claimed is:

1. A method of classification of a hydrocarbon mixture, the method comprising:
  performing two-dimensional gas chromatography on the hydrocarbon mixture to obtain a chromatogram displaying peaks associated with hydrocarbons within the hydrocarbon mixture using a two-dimensional gas chromatograph (GC×GC) system comprising a flame ionization detector (FID), a reversed phase column configuration with a primary mid-polar or polar column and a secondary non-polar column, and a standard mixture of hydrocarbon compounds;

using gas chromatography imaging and data processing software, performing a classification process to group the hydrocarbons displayed in the chromatogram into groups with the same carbon number from the same hydrocarbon class, wherein the groups are identified and labeled based on hydrocarbon peaks associated with the standard mixture; and performing a quantification process that includes summing the peak areas of the hydrocarbons in each group classified in the chromatogram to determine a total peak area of each group and then calculating the weight percent of each group by dividing the total peak area of the group by the total peak area of the hydrocarbon mixture;

wherein the classification process is performed without using mass spectrometry.

2. The method of claim 1, wherein the standard mixture consists of a plurality of the following twenty-four hydrocarbon compounds: n-octane, n-dodecane, n-hexadecane, perhydrophenalene, tetradecahydroanthracene, toluene, ethylbenzene, n-propylbenzene, n-butylbenzene, n-hexylbenzene, indan, 4,7-dimethylindan, 1,1-dimethyltetralin, 1,1,6-trimethyltetralin, naphthalene, 2-methylnaphthalene, 1,8-dimethylnaphthalene, biphenyl, 4-methylbiphenyl, 4,4-dimethylbiphenyl, phenanthrene, 1-methylanthracene, pyrene, and 1-methylpyrene.

3. The method of claim 1, wherein the standard mixture consists of the following hydrocarbon compounds: n-octane, n-dodecane, n-hexadecane, perhydrophenalene, tetradecahydroanthracene, toluene, ethylbenzene, n-propylbenzene, n-butylbenzene, n-hexylbenzene, indan, 4,7-dimethylindan, 1,1-dimethyltetralin, 1,1,6-trimethyltetralin, naphthalene, 2-methylnaphthalene, 1,8-dimethylnaphthalene, biphenyl, 4-methylbiphenyl, 4,4-dimethylbiphenyl, phenanthrene, 1-methylanthracene, pyrene, and 1-methylpyrene.

4. The method of claim 3, wherein the classification process includes grouping isoparaffins by:

viewing the second chromatogram in the gas chromatography imaging and data processing software with the borders corresponding to the n-paraffins overlaid thereon;

adjusting the colors of the second chromatogram to isolate isoparaffins; and overlaying borders on the second chromatogram corresponding to groups of the isoparaffins, wherein the borders are determined based on peak locations of the isoparaffins which elute between and/or above the n-paraffins and directly to the left of a corresponding one of the n-paraffins having the same carbon number as the carbon number of the respective one of the groups of the isoparaffins.

5. The method of claim 4, wherein the classification process includes grouping monocycloparaffins by:

viewing the second chromatogram in the gas chromatography imaging and data processing software with the borders corresponding to the groups of the n-paraffins and isoparaffins overlaid thereon;

adjusting the colors of the second chromatogram to isolate monocycloparaffins; and overlaying borders on the second chromatogram corresponding to groups of the monocycloparaffins, wherein the borders are determined based on peak locations of the monocycloparaffins which elute between and/or below the n-paraffins and directly to the right of a corresponding one of the n-paraffins having the same carbon number as the carbon number of the respective one of the groups of monocycloparaffins, wherein the borders of the n-paraffins and the groups of the monocycloparaffins of the same carbon number intercept.

6. The method of claim 5, wherein the classification process includes grouping dicycloparaffins by:

viewing the second chromatogram in the gas chromatography imaging and data processing software with the borders corresponding to the groups of the n-paraffins, isoparaffins, and monocycloparaffins overlaid thereon;

adjusting the colors of the second chromatogram to isolate dicycloparaffins;

overlaying borders on the second chromatogram corresponding to groups of the dicycloparaffins, wherein the borders are determined based on peak locations of the dicycloparaffins which elute directly to the right of a corresponding one of the groups of monocycloparaffins having a carbon number one less than the carbon number of the respective one of the groups of the dicycloparaffins.

7. The method of claim 6, wherein the classification process includes grouping tricycloparaffins by:

viewing the first chromatogram in the gas chromatography imaging and data processing software;

identifying and labeling peaks associated with perhydrophenalene and tetradecahydroanthracene;

viewing the second chromatogram in the gas chromatography imaging and data processing software with the borders corresponding to the n-paraffins, isoparaffins, monocycloparaffins, and dicycloparaffins and the peaks associated with perhydrophenalene and tetradecahydroanthracene overlaid thereon; and overlaying borders on the second chromatogram corresponding to groups of the tricycloparaffins, wherein the borders are determined based on peak locations of the tricycloparaffins which elute directly to the right of a corresponding one of the groups of the dicycloparaffins having a carbon number one less than the carbon number of the respective one of the groups of the tricycloparaffins and by using the peaks associated with perhydrophenalene and tetradecahydroanthracene as visual aids.

8. The method of claim 7, wherein the classification process includes grouping alkylbenzenes by:

viewing the first chromatogram in the gas chromatography imaging and data processing software;

identifying and labeling peaks associated with toluene, ethylbenzene, n-propylbenzene, n-butylbenzene, and n-hexylbenzene;

viewing the second chromatogram in the gas chromatography imaging and data processing software with the borders corresponding to the groups of the n-paraffins, isoparaffins, monocycloparaffins, dicycloparaffins, and tricycloparaffins and the peaks associated with toluene, ethylbenzene, n-propylbenzene, n-butylbenzene, and n-hexylbenzene overlaid thereon; and overlaying borders on the second chromatogram corresponding to groups of the alkylbenzenes, wherein the peaks associated with toluene, ethylbenzene, n-propylbenzene, n-butylbenzene, and n-hexylbenzene are used as visual aids for overlaying the borders of the groups of the alkylbenzenes.

9. The method of claim 8, wherein the classification process includes grouping cycloaromatics by:

viewing the first chromatogram in the gas chromatography imaging and data processing software;
identifying and labeling peaks associated with indan, 4,7-dimethylindan, 1,1-dimethyltetralin, and 1,1,6-trimethyltetralin;
viewing the second chromatogram in the gas chromatography imaging and data processing software with the borders corresponding to the groups of the n-paraffins, isoparaffins, monocycloparaffins, dicycloparaffins, tricycloparaffins, and alkylbenzenes and the peaks associated with indan, 4,7-dimethylindan, 1,1-dimethyltetralin, and 1,1,6-trimethyltetralin overlaid thereon; and
overlaying borders on the second chromatogram corresponding to groups of the cycloaromatics, wherein the borders are determined based on peak locations of the cycloaromatics which elute directly to the right of a corresponding one of the groups of the alkylbenzenes having the same carbon number as the carbon number of the respective one of the groups of the cycloaromatics and by using the peaks associated with indan, 4,7-dimethylindan, 1,1-dimethyltetralin, and 1,1,6-trimethyltetralin as visual aids.

10. The method of claim 9, wherein the classification process includes grouping alkynaphthalenes by:
viewing the first chromatogram in the gas chromatography imaging and data processing software;
identifying and labeling peaks associated with naphthalene, 2-methylnaphthalene, and 1,8-dimethylnaphthalene;
viewing the second chromatogram in the gas chromatography imaging and data processing software with the borders corresponding to the groups of the n-paraffins, isoparaffins, monocycloparaffins, dicycloparaffins, tricycloparaffins, alkylbenzenes, and cycloaromatics and the peaks associated with naphthalene, 2-methylnaphthalene, and 1,8-dimethylnaphthalene overlaid thereon; and
overlaying borders on the second chromatogram corresponding to groups of the alkynaphthalenes, wherein the borders are determined based on peak locations of the alkynaphthalenes which elute directly to the right of a corresponding one of the groups of the cycloaromatics having the same carbon number as the carbon number of the respective one of the groups of the alkynaphthalenes and by using the peaks associated with naphthalene, 2-methylnaphthalene, and 1,8-dimethylnaphthalene as visual aids.

11. The method of claim 10, wherein the classification process includes grouping biphenyls by:
viewing the first chromatogram in the gas chromatography imaging and data processing software;
identifying and labeling peaks associated with biphenyl, 4-methylbiphenyl, and 4,4-dimethylbiphenyl;
viewing the second chromatogram in the gas chromatography imaging and data processing software with the borders corresponding to the groups of the n-paraffins, isoparaffins, monocycloparaffins, dicycloparaffins, tricycloparaffins, alkylbenzenes, cycloaromatics, and alkynaphthalenes and the peaks associated with biphenyl, 4-methylbiphenyl, and 4,4-dimethylbiphenyl overlaid thereon; and
overlaying borders on the second chromatogram corresponding to groups of the biphenyls, wherein the borders are determined based on peak locations of the biphenyls which elute directly to the right of a corresponding one of the groups of the alkynaphthalenes having a carbon number one less than the carbon number of the respective one of the groups of the biphenyls and by using the peaks associated with biphenyl, 4-methylbiphenyl, and 4,4-dimethylbiphenyl as visual aids.

12. The method of claim 11, wherein the classification process includes grouping anthracenes and phenanthrenes by:
viewing the first chromatogram in the gas chromatography imaging and data processing software;
identifying and labeling peaks associated with phenanthrene and 1-methylanthracene;
viewing the second chromatogram in the gas chromatography imaging and data processing software with the borders corresponding to the groups of the n-paraffins, isoparaffins, monocycloparaffins, dicycloparaffins, tricycloparaffins, alkylbenzenes, cycloaromatics, alkynaphthalenes, and biphenyls and the peaks associated with phenanthrene and 1-methylanthracene overlaid thereon; and
overlaying borders on the second chromatogram corresponding to groups of the anthracenes and phenanthrenes, wherein the borders are determined based on peak locations of the anthracenes and phenanthrenes which elute directly to the right of a corresponding one of the groups of the biphenyls having a carbon number one less than the carbon number of the respective one of the groups of the anthracenes and phenanthrenes and by using the peaks associated with phenanthrene and 1-methylanthracene as visual aids.

13. The method of claim 12, wherein the classification process includes grouping pyrenes by:
viewing the first chromatogram in the gas chromatography imaging and data processing software;
identifying and labeling peaks associated with phenanthrene and 1-methylanthracene;
viewing the second chromatogram in the gas chromatography imaging and data processing software with the borders corresponding to the groups of the n-paraffins, isoparaffins, monocycloparaffins, dicycloparaffins, tricycloparaffins, alkylbenzenes, cycloaromatics, alkynaphthalenes, biphenyls, anthracenes, and phenanthrenes and the peaks associated with phenanthrene and 1-methylanthracene overlaid thereon; and
overlaying borders on the second chromatogram corresponding to groups of the pyrenes, wherein the borders are determined based on peak locations of the pyrenes which elute directly to the right of a corresponding one of the groups of the anthracenes and phenanthrenes having the same carbon number as the carbon number of the respective one of the groups of the pyrenes and by using the peaks associated with phenanthrene and 1-methylanthracene as visual aids.

14. The method of claim 1, wherein the classification process includes grouping n-paraffins by:
viewing a first chromatogram of the standard mixture in the gas chromatography imaging and data processing software, wherein hydrocarbons are displayed with increasing carbon number from left to right across the first chromatogram;
identifying n-paraffins in the first chromatogram to establish peak locations for use as n-paraffin standards;
overlaying borders on the first chromatogram corresponding to the n-paraffin standards;
viewing a second chromatogram of the hydrocarbon mixture in the gas chromatography imaging and data processing software wherein hydrocarbons are displayed with increasing carbon number from left to right across the second chromatogram and the borders corresponding to the n-paraffin standards are overlaid thereon;

adjusting the colors of the second chromatogram to isolate n-paraffins displayed thereon; and identifying and labeling groups of the n-paraffins displayed in the second chromatogram based on the borders drawn corresponding to the n-paraffin standards.

15. The method of claim 1, wherein the hydrocarbon mixture has a carbon number in a range of C6 through C33.

16. The method of claim 1, wherein the hydrocarbon mixture is an aviation fuel.

17. The method of claim 1, wherein the hydrocarbon mixture is a diesel fuel.

18. The method of claim 1, wherein the GC×GC system does not comprise a mass spectrometer.

* * * * *